US007041209B1

(12) United States Patent
Pizzariello et al.

(10) Patent No.: US 7,041,209 B1
(45) Date of Patent: May 9, 2006

(54) PH-SENSITIVE AMPEROMETRIC BIOSENSOR

(75) Inventors: Andrea Pizzariello, Silea (IT); Miroslav Stredansky, Modra (SK); Silvia Stredanska, Modra (SK); Stanislav Miertus, Bratislava (SK)

(73) Assignee: Saicom S.R.I., Trieste (IT)

( * ) Notice: Subject to any disclaimer, the term of this patent is extended or adjusted under 35 U.S.C. 154(b) by 0 days.

(21) Appl. No.: 09/890,478

(22) PCT Filed: Jan. 21, 2000

(86) PCT No.: PCT/EP00/00455

§ 371 (c)(1),
(2), (4) Date: Jul. 31, 2001

(87) PCT Pub. No.: WO00/46393

PCT Pub. Date: Aug. 10, 2000

(30) Foreign Application Priority Data

Feb. 4, 1999 (IT) ................................ MI99A0210

(51) Int. Cl.
*G01N 27/327* (2006.01)
(52) U.S. Cl. ................................ 205/777.5; 205/787.5; 204/403.14; 204/433
(58) Field of Classification Search ................................
204/403.01–403.14, 433; 205/777.5, 778, 205/787.5, 792
See application file for complete search history.

(56) References Cited

U.S. PATENT DOCUMENTS 5,795,953 A * 8/1998 Kim et al. .................. 526/258

FOREIGN PATENT DOCUMENTS

EP 0 125139 11/1984
WO WO 91/16630 10/1991

OTHER PUBLICATIONS

ACS Registry entry for Meldola Blue.*
Karalemas et al. ("Construction of L-lysine biosnesor by immobilizng lysine oxidase on a gold-poly(o-phenylenediamine) electrode," Talanta 53 (2000) 391-402).*
Lobo et al. ("Electrocatalytic detection of nicotinamide coenzymes by poly(p-amiophenol)- and poly(-phenylenediamine)-modified carbon paste electrodes," Analytica Chimica Acta 325 (1996) 33-42).*
Kulys J. et al.: "Methylene-Green-mediated carbon paste glucose sensor" Electroanalysis, vol. 7, No. 1, 1995, pp. 92-94.
Chi Q. et al.: "Electrocatalytic oxidation of reduced nicotinamide coenzymes at Methylene Green-modified electrodes and fabrication of amperometric alcohol biosensors" Anal. Chimica Acta, vol. 285, 1994, pp. 125-133.

(Continued)

*Primary Examiner*—Alex Noguerola
(74) *Attorney, Agent, or Firm*—Stetina Brunda Garred & Brucker

(57) ABSTRACT

The present invention describes a new electrochemical biosensor comprising (i) a biocatalyst producing a pH change when interacting with the analyte to be determined and (ii) a compound exhibiting different redox properties both in its protonated and non-protonated forms (pH-sensitive redox compound). The elements described above are integrated in a biosensor system composed of a working electrode and a reference electrode connected to an ammeter. When the analyte is present, the system produces a current change that is proportional to the concentration of the analyte. The biosensors described herein can be used in the accurate detection of a wide range of analytes. They can be used in diagnostics, industrial processes, food and feed quality control, biotechnology, pharmaceutical industry, environmental monitoring and so on.

12 Claims, 8 Drawing Sheets

OTHER PUBLICATIONS

Qian J et al.: "An amperometric new methylene blue N-mediating sensor for hydrogen peroxide based on regenerated silk fibroin as an immobilization matrix for peroxidase;" Anal. Biochem.: (1996) 236, 2, 208-14.

Lobo Castanon M J et al: "Amperometric detection of ethanol with poly-(ophenylenediamine)) modified enzyme electroes;" Biosensors Bioelectron.: (1997) 12, 6.

Wang J. et al.: "Amperometric biosensing of organic peroxides with peroxidase-modified electrodes": Anal:. Chimica Acta, vol. 254, 1991, pp. 81-88.

Kuly J. et al.: "Glucose biosensor based on the incorporation of Meldola Bllue and glucose oxidase within carbon paste" Anal. Chimica Acta, vol. 288, 1994, pp. 193-196.

Groton L. et al.: "Amperometric glucose sensors based on immobilised glucose-oxidizing enzymes and chemically modified electrodes" Anal. Chimica Acta, vol. 249, 1991, pp. 43-54.

Stredansky M. et al: "Amperometric pH-sensing biosensors for urea, penicillin and oxalacetate" Analytica Chimica Acta, (Jun. 30, 2000) vol. 415, No. 1-2, pp. 151-157.

Blackburn "Chemically Sensitive Field Effect Transistors", in Biosensors, Fundamentals and Applications, A.P.F. Turner, I. Karube and G.S. Wilson Ed., Oxford Univ. Press (pp. 481-530) 1987.

Contractor, et al. "Conducting Polymer-Based Biosensors" Electrochimica Acta, vol. 39, No. 8/9, (pp. 1321-1324) ,1994.

Gorton "Carbon Paste Electrodes Modified With Enzymes, Tissues, And Cells" Electroanalysis, 7, No. 1 (pp. 23-45), 1995.

Kuan, et al. "Ion-Selective Electrodes And Biosensors Based On ISEs", in Biosensors, Fundamentals and Applications, A.P.F. Turner, I, Karube and G.S. Wilson Ed) (pp. 135-152), 1987.

Laranjeira, et al. "A Conductimetric System Based On Polyaniline For Determination Of Ammonia In Fertilizers", Anal. Lett, 30, (pp. 2189-2209), 1997.

Nishizawa, et al "Penicillin Sensor Based On a Microarray Electrode Coated With PH-Responsive Polypyrrole" Anal. Chem., 64, (pp. 2642-2644), 1992.

Palleschi, et al "Bioelectrochemical Determination Of Lactic And Malic Acids In Wine", Talanta vol. 41, No. 6, (pp. 917-923), 1994.

Wilson—"Fundamentals of Amperometric Sensors" (Biosensors, Fundamentals and Applications A.P.F. Turner, I. Karube and G.S. Wilson Ed.), Oxford Univ Press, (pp. 165-179), 1987.

* cited by examiner

PH-SENSITIVE AMPEROMETRIC BIOSENSOR

FIELD OF THE INVENTION

The present invention relates to the field of electrochemical analysis. It refers specifically to systems for the electrochemical detection of analytes based on the activity of biocatalysts. The object of this invention is a new group of biosensors and their use in a method for the detection of analytes.

PRIOR ART

A biosensor is a device that embodies a biological sensing element that is either connected to or inserted into a transducer. The aim is the production of electronic signals proportional to the concentration of the specific substance that has to be determined.

The advent of biosensors has provided an interesting alternative to conventional laboratory analysis. Due to their simple manipulation, compactness and versatility of use, biosensors allow for easy performances of on-site tests. Specific and sensitive devices have been used in medical diagnostics, quality assessment of food, environmental monitoring, fermentation techniques, analytical control and so on.

Electrochemical biosensors, specifically the amperometric ones, play a significant role in the use of these detection devices.

Amperometric biosensors produce a linear signal and are featured by high sensitivity. Under favourable conditions, analyte concentrations ranging from $1\times10^{-8}$ to $1\times10^{-9}$ M can be detected and a dynamic range from three to four order of magnitudes can be easily obtained (G. S. Wilson, in "Biosensors, Fundamentals and Applications," A. P. F. Turner, I. Karube and G. S. Wilson Ed., Oxford Univ. Press, 165–179, 1987).

The first generation of amperometric biosensors is based on the oxidation of the analyte by oxidases (biocatalysts) using oxygen as an electron acceptor. As a consequence, either the reduction in the oxygen concentration or the increase in the produced hydrogen peroxide concentration are measured by an electrode in the form of current that is proportional to the analyte concentration.

In the second generation systems, the enzyme performs the first redox reaction with the substrate (the analyte) but is then reoxidised by a redox mediator as opposed to oxygen; the mediator is then oxidised by the electrode and the corresponding amperometric signal is measured. Many examples of mediators containing biosensors are quoted in a review by Gorton (Electroanalysis, 7, 23–45, 1995).

Since the redox mediators shuttle electrons that come to the redox centre of the biocatalyst from the substrate to the working electrode, a limitation inherent in these amperometric biosensors consists in the use of the biocatalysts belonging to the oxidoreductase group. As a consequence, these biosensors can detect of a limited group of analytes.

A certain number of enzymes belonging to the groups of hydrolases, transferases, oxidoreductases, lyases, ligases, and in particular decarboxylases, phosphorylases, esterases, phosphatases, deaminases, kinases, changes the concentration of $H^+$ ions (by either consumption or production) by their biocatalytic interaction with a substrate and this change depends on the substrate concentration. These biocatalysts, combined with a suitable potentiometric transducer (for example the typical glass pH electrode or with the solid and liquid membrane pH electrode) are used for the implementation of potentiometric biosensors. Examples of analytes that are determined by these biosensors are urea, penicillin, glucose, malate (S. S. Kuan and G. G. Guibault, In: Biosensors, Fundamentals and Applications, A. P. F. Turner, I. Karube and G. S. Wilson Ed., Oxford Univ. Press, 135–152, 1987; Palleschi et al., Talanta, 41, 917–923, 1994). The disadvantages of these biosensors consist in a logarithmic response and in a low sensitivity. Their useful analytical range is generally from $1\times10^{-1}$ to $1\times10^{-4}$ M, exceptionally to $1\times10^{-5}$ M.

Another group of potentiometric biosensors uses a combination of biocatalysts that modify their pH when interfaced with ion-sensitive field effect transistors (ISFET). ISFET are prepared with a manufacturing procedure based on silicon where the silicon nitride layer deposited on the surface is mostly used as a pH-sensitive transducer. Some examples consist in biosensors for the detection of urea, ATP, penicillin, glucose and acetylcholine (G. F. Blackburn, In: Biosensors, Fundamentals and Applications, A. P. F. Turner, I. Karube and G. S. Wilson Ed., Oxford University Press, 481–530, 1987).

The drawbacks inherent in these biosensor consist in a low sensitivity (measurable response in concentration range from $1\times10^{-1}$ to $1\times10^{-4}$ M), high costs and a complex manufacturing procedure.

Recently, a new group of electrochemical biosensors based on the combination of a biocatalyst that modifies the pH and a conductometric transducer (A. Q. Contractor et al., Electrochim. Acta, 39, 1321–1324, 1994; J. M. Goncalves Laranjeira et al, Anal. Lett. 30, 2189–2209, 1994; Nishizawa et al., Anal. Chem., 64, 2642–2644, 1992) has been described. This new kind of biosensors exploits the pH effect on the electric properties of a conductive polymer (polyaniline, polypyrrole) deposited on the electrode surface. They consist in two platinum electrodes that are placed at a distance of several μm and covered by the conductive polymer film and an enzymatic membrane. With this kind of biosensor it is possible to detect analytes such as urea, glucose, lipids, haemoglobin and penicillin. These biosensors provide a fast response and an improved sensitivity with respect to the potentiometric biosensors (the useful analytical range goes from $1\times10^{-1}$ to $1\times10^{-5}$ M, in the best cases $1\times10^{-6}$ M); however, their sensitivity is still far from the one that can be obtained with amperometric biosensors. Moreover, they require an accurate and expensive manufacturing procedure. As a consequence, in view of the drawbacks listed previously, it is necessary to identify alternative electrochemical biosensors with higher sensitivity and an easier manufacturing procedure.

SUMMARY OF THE INVENTION

The present invention describes a new electrochemical biosensor comprising (i) a biocatalyst producing a pH change when interacting with the analyte to be determined and (ii) a compound exhibiting different redox properties both in its protonated and non-protonated forms (pH-sensitive redox compound). The elements described above are integrated in a biosensor system composed of a working electrode and a reference electrode connected to an ammeter. When the analyte is present, the system produces a current change that is proportional to the concentration of the analyte. The biosensors described herein can be used in the accurate detection of a wide range of analytes. They can be used in diagnostics, industrial processes, food and feed quality control, biotechnology, pharmaceutical industry, environmental monitoring and so on.

DESCRIPTION OF FIGURES

FIG. 1: platinum electrode; dissolved hematein at the concentration of 0.5 mM (curve a) and 2.5 mM (curve b);

FIG. 2: dissolved hematein; carbon paste electrode (curve a) and solid composite electrode (curve b);

FIG. 3: golden electrode with methylene blue monolayer;

FIG. 4: solid composite electrode; dissolved hematoxylin (curve a), dissolved quercitin (curve b), dissolved harmaline (curve c);

FIG. 5: solid composite electrode with electropolymerised orto-phenylendiamine;

FIG. 6: platinum electrode with electropolymerised pyrogallol;

FIG. 7: solid composite electrode modified with laurylgallate;

FIG. 8: biosensor for the detection of urea, dissolved hematein, platinum electrode (curve a) or solid composite electrode (curve b);

FIG. 9: biosensor for the detection of urea, dissolved hematein, solid composite electrode containing urease, in the presence of either 5 mM (curve a) or 1 mM (curve b) phosphate buffer;

FIG. 10: biosensor for the detection of urea, solid composite electrode modified with alkylgallate;

FIG. 11: biosensor for the detection of oxaloacetate, dissolved hematein, solid composite electrode;

FIG. 12: biosensor for the detection of glucose, solid composite electrode modified with poly(ortho-phenylendiamine) film;

FIG. 13: biosensor for the detection of hydrogencarbonate, dissolved hematein, platinum electrode;

FIG. 14: biosensor for the detection of penicillin, dissolved hematein, platinum electrode;

FIG. 15: biosensor for the detection of ATP, dissolved hematein, platinum electrode;

FIG. 16: biosensor for the detection of urea, golden electrode with methylene blue monolayer.

DETAILED DESCRIPTION OF THE INVENTION

Figure 1:
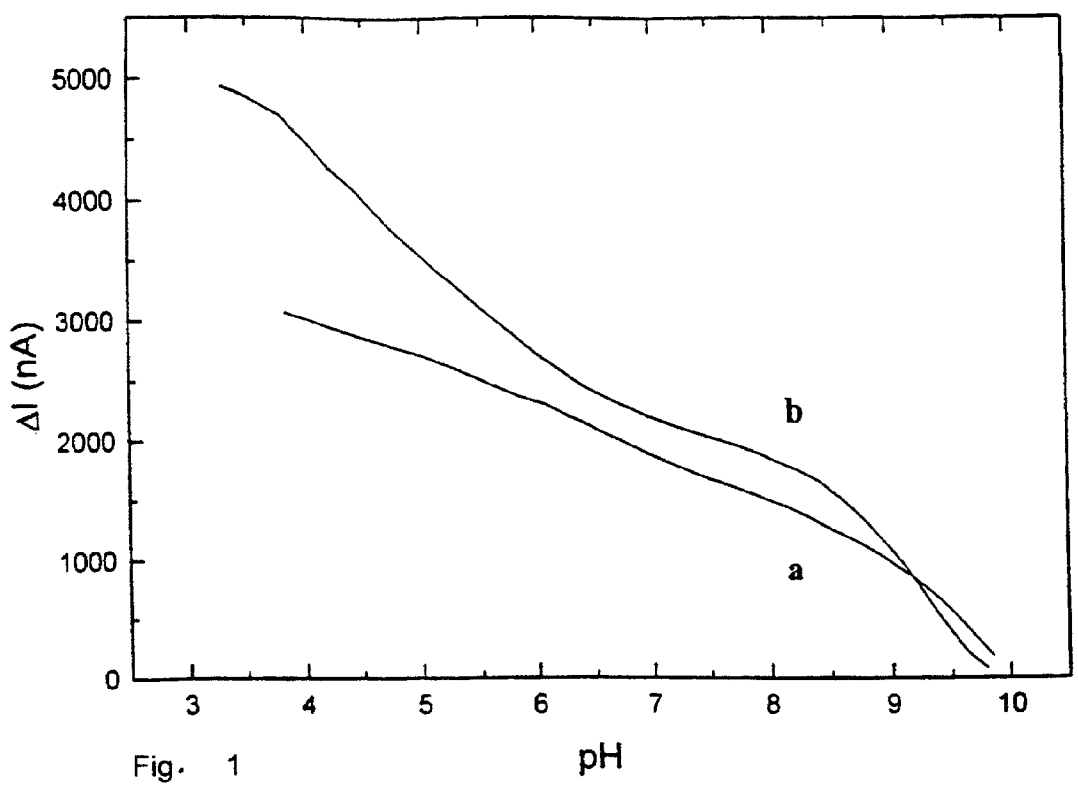
FIGS. 1–7 show the current change dependency on pH at suitable constant potentials using several pH-sensitive redox compounds and various electrodes as described in Examples 1–7.

The object of the present invention is an amperometric biosensor system for the detection of analytes comprising:
- at least one biocatalyst producing a pH change by its interaction with the analyte to be determined;
- at least one compound exhibiting different redox properties both in its protonated and non-protonated forms. Said compound will be hereinafter indicated as "pH-sensitive redox compound";
- a working electrode;
- a reference electrode.

The electrodes at c) and d) are connected through an ammeter.

In one embodiment of this invention, the biocatalyst (a) and the pH-sensitive redox compounds (b) are contained in the working electrode; as an alternative, one or more of these components are present in the measuring solution in which the electrodes are immersed.

The biosensor of this invention can optionally be covered with a suitable semipermeable membrane.

The working principle of these biosensors is described hereinafter. The electrodes are immersed into a measuring solution and a suitable potential is applied between them. The electrode reaction is carried out up to reaching the equilibrium between the oxidised and the reduced form of the pH-sensitive redox compound (b). This electrochemical reaction is accompanied by an electron flow measured in the form of electric current by the ammeter. Up to this stage, the biocatalyst (a) is not involved. Once the sample containing the analyte is added to the solution, the biocatalyst/analyte reaction takes place and the pH is modified accordingly; the pH variation modifies the equilibrium of the protonated/non-protonated forms of the redox compound (b). Since these forms of the redox compound exhibit different redox properties, any changes in their concentration produce a current change at the constant potential applied. The current change is monitored by the ammeter and depends on the substrate concentration.

As regards the nature of this biocatalyst (a), it can be any biological entity capable of interacting with the analyte to be determined and causing a pH variation as a result of such interaction. As a matter of fact, any biocatalyst reacting with its normal substrate either producing or consuming $H^+$ ions can be used as a biocatalyst for the detection of that substrate. Suitable biocatalysts are, for example, enzymes catalyzing reactions that involve either the production or the consumption of $H^+$ ions; typical examples are hydrolases, oxidoreductases, transferases, lyases, ligases and preferably phosphorylases, decarboxylases, esterases, proteinases, deaminases, amidases, phosphatases, and synthetases. Other examples of biocatalysts with the same features are to be found among imunoproteins, nucleic acids, sinzymes, catalytic antibodies.

Other pH changing biocatalysts can be found among biological structures or biological aggregates such as cells or cell fragments, tissues, organelles and their fragments, fractions, homogenates, extracts, lysates.

It is possible to use one single biocatalyst or a mixture of two or more of them. The choice of the suitable biocatalysts is determined by the nature of the analyte itself, according to the principle whereby any analyte works as a substrate for a given biocatalyst: for example, esterases are indicated for the analytical detection of esters; decarboxylases are used for the detection of carboxylic acids, deaminases for amines and so on.

Examples of preferred biocatalysts for the present invention are: urease, oxalacetate decarboxylase, glucose oxidase, carbonic anhydrase, penicillinase, apyrase for the detection respectively of urea, oxalacetate, glucose, hydrogencarbonate, penicillin, ATP.

In the biosensors of the invention, the biocatalysts (a) can be incorporated in the working electrode or otherwise can be present in the measuring solution in either a dispersed or soluble form.

The incorporation of said biocatalyst in the working electrode is particularly suited for the preparation of composite biosensors: these biosensors are especially preferred.

Said biocatalysts can also be applied onto the surface of the working electrodes. In this case, they are normally immobilized by means of physical or chemical methods. The preferred methods for immobilization consist in one or more among: covering with a semipermeable membrane, entrapping in a polymer or in a gel layer, crosslinking with bifunctional agents, covalent binding, adsorption, and immobilization in the outer membrane.

The biocatalyst is normally placed in the measuring solution by dissolving the biocatalyst in the solution or by dispersing it homogeneously. This is particularly indicated for disposable thick-layer biosensors, where the biocatalyst is dissolved in the whole volume of the sample added. It is devised specifically for biosensors that determine polymeric analytes since it avoids steric hindrances that could occur when the biocatalyst is immobilized. Another possible way of placing the biocatalyst in the biosensor of the invention consists in its immobilization in a small bioreactor inserted in front of the working electrode when the flow system is applied.

When the activity of the biocatalyst requires the presence of a cofactor, for example a coenzyme or an activator, the biosensors of this invention include also said cofactor. The cofactor is preferably placed together with the biocatalyst, i.e. they are either placed onto the electrode surface, or in the electrode body or in the solution.

A further element of the biosensor system according to the present invention is represented by the pH-sensitive redox compound (b). These are compounds that are present in solution in equilibrium between the protonated and the non-protonated form having different redox potentials.

The pH-sensitive redox compounds are selected in the group consisting of cyclic hydrocarbons containing from 4 to 30 carbon atoms and susbstituted with at least one group selected from —OH, —SH, —NH$_2$, =O, =S, =NH, —OR$_1$, —SR$_1$, —NHR$_1$, —NR$_1$R$_2$, =NR$_1$, where R$_1$ and R$_2$ are hydrocarbon chains optionally further substituted, or selected in the group consisting of heterocyclic compounds containing from 3 to 30 carbon atoms and one or more heteroatoms selected in the group consisting of N, S, O, Se, Te, B, P, As, Sb, Si, optionally substituted with a group selected from —OH, —SH, —NH$_2$, =O, =S, =NH, —OR, —SR$_1$, —NHR$_1$, — NR$_1$R$_2$, =NR$_1$, where R$_1$ and R$_2$ are independent hydrocarbon chains. These compound can be selected in the form of either monomer, or oligomer or polymer. The above mentioned compounds can be used either alone or in a mixture with one or more of them.

The preferred classes of pH-sensitive redox compounds are indicators of pH (ie. hematoxylin, hematein), phenoxazine and phenothiazine dyes (i.e. methylene blue), natural antioxidants (i.e. quercitin, flavonoids, alkylgallates) polymerised ortho-phenylendiamine or para-phenylendiamine.

According to the invention, the pH-sensitive redox compound is present in the working electrode or dissolved in the measuring solution. The pH sensitive redox compounds that are water soluble are preferably added to the solution; those insoluble in water are preferably used to modify the working electrode.

When present in the working electrode, the pH-sensitive redox compound can be deposited onto its surface in a free form; otherwise, it can be chemically or physically bound (immobilized) onto the working electrode surface; or alternatively it can be a component of the body of a composite working electrode.

If the pH-sensitive redox compound is either a polymer or an oligomer, this can be prepared also in siftu on the working electrode by chemical or physical polymerization, preferably by radical polymerization, electropolymerization or photopolymerization.

Among the redox compounds quoted above, phenothiazines dyes and poly(ortho- phenylendiamine) are particularly suited to be either physically or chemically bound to the electrode surface. Hematein, hematoxillin, phenothiazines dyes and quercitin are particularly indicated to be added to the measuring solution. Alkylgallates are preferably suited to be incorporated in the biosensor's body as components of a composite working electrode.

Several working electrodes can be used as element (c) of the biosensor system of this invention. Said working electrodes are selected in the group consisting of the typical working electrodes used in amperometry (like, for example, platinum, gold, mercury, glassy carbon electrodes) or by composite electrodes (such as for example the solid composite electrodes).

For the purpose of the present invention, by the term "solid composite electrodes" are meant the electrodes described in WO 97/02359, hereby incorporated by reference.

Similarly, reference electrodes useful as element (d) of the biosensor of this invention are commonly available in amperometry. The preferred reference electrodes are standard calomel electrodes (SCE) and Ag/AgCl electrodes. The Ag/AgCl electrodes are particularly suitable because they can be designed in various forms like for example wire disc, layer or bar.

The working potential to be applied between the two electrodes is preferably about 0.0 mV or it is negative (versus Ag/AgCl reference electrode). The application of this potential significantly reduces possible electrochemical interferences deriving from easily oxidizable interfering compounds present in real samples.

Differently from the typical amperometric biosensors, where the measurements are carried out in strongly buffered solutions requiring a constant pH, in the present invention the measurements are carried out in non-buffered solutions or in solutions having a low buffering capacity. If a solution having low buffering capacity is used, the preferred concentration of the buffering compounds ranges from 0.5 to 20 mM.

The term "measuring solution" used in this invention is not strictly limited to systems where all components are dissolved; it also includes liquid systems where at least part of the components are contained in a homogeneously dispersed status such as suspensions, emulsions and so on. The biosensor implemented as described in the present invention can amperometrically determine many more analytes than was possible so far.

The biosensor system according to the present invention shows better performances in term of detection limit, linearity of the output signal, rapidity of response, selectivity and stability of those reported in literature. Besides the good specificity and sensitivity, a simple manufacturing procedure and a versatile design represent also relevant advantages of the biosensor system of the present invention. The biosensor's sensitivity described hereinafter (see Examples) ranges from 0.1 to 5 $\mu$A mM$^{-1}$ cm$^{-2}$ and the detection limits range from $1\times10^{-5}$ to $1\times10^{-7}$ M.

The biosensors of the present invention are versatile with respect to the biocatalyst, the pH-sensitive redox compounds, the working and reference electrodes and the setting of the biosensor. They can also have a good variability in the design and can be shaped in many different forms such as for example, strips, tips and needles. Disc, tube, wire, thick layer, thin layer and other forms of the electrodes fit perfectly in the biosensor described in this invention. The preparation of microelectrodes according to the present invention is also possible. The biosensor system according to the present invention can be profitably used in human and veterinary diagnostics, industrial processes, agro-food industry, biotechnology, pharmaceutical industry, environmental monitoring and so on. All these possible uses are included in the present invention.

A further embodiment of the present invention concerns a method for the determination of the analytes concentration characterised by the use of the new biosensors described previously.

A preferred method for the determination includes the following steps:
(a) placing the electrodes in a measuring solution;
(b) applying a suitable potential between the electrodes;
(c) measuring a background current;
(d) adding to the solution the sample containing the analyte to be determined;
(e) measuring the current change that is proportional to the analyte concentration;
(f) optionally subtracting the current change measured with a blank electrode from the value obtained in (e).

Step (f) is added so as to eliminate possible interferences. The blank electrode differs from a normal working electrode as described so far, only in as much as it either contains said biocatalysts in a non-active form or it does not contain them at all. The procedure for obtaining a current change measured with the blank electrode is the same as the one described in steps (a)–(e).

All readings are carried out when the sample is uniformly diluted in the measuring solution and the signal is stable.

As described above, the invention is compatible with several biosensor designs, such as tips, needles, strips and so on. Some of these forms (see strip biosensor) work in absence of a measuring solution and react immediately upon contact with the sample containing the analyte. This contact occurs for example when a drop of the sample containing the analyte is added to the biosensor, on the biosensor or by plunging the biosensor itself in the solution. In these cases, the method for the detection of the analyte is modified in the following way:
(a) applying a suitable potential between the electrodes;
(b) measuring a background current;
(c) contacting the biosensor with the sample containing the analyte;
(d) measuring a current change that is proportional to the analyte concentration;
(e) optionally subtracting the current change measured with a blank electrode from the value obtained in (d).

The methods described above can be either qualitative (they determine the presence of the analyte in the solution) or quantitative (they determine the analyte concentration) since the current change is proportional to the analyte concentration.

So far, the biocatalyst has been defined to react positively with the analyte and thereby cause a pH change. In a further embodiment of this invention, the system identifies the presence of an analyte that is an inhibitor of the biocatalyst, thereafter called inhibiting-analyte. In this case, the interaction turns out to be negative and the current change depending on the extent of the inhibition will be proportional to the inhibiting-analyte concentration.

This aspect further broadens the range of analytes that can be identified with the biosensors of the present invention; each substance acting as the inhibitor of a pH-changing biocatalyst can be identified in this way.

With the purpose of implementing this aspect of the invention, the measurement method is partly modified by adding the normal substrate of the biocatalyst to the system before introducing the sample containing the inhibiting-analyte that has to be tested. As a consequence, the method comprises the following steps:
(a) placing the electrodes in a measuring solution;
(b) applying a suitable potential between the electrodes;
(c) adding the substrate of said biocatalyst to the measuring solution;
(d) measuring a background current;
(e) adding to the solution the sample containing the inhibiting-analyte to be determined;
(f) measuring a current change that is proportional to the inhibiting-analyte concentration;
(g) optionally subtracting the current change measured with a blank electrode from the value obtained in (f).

If the biosensor's design (e.g. strip biosensor) allows to work in absence of a measuring solution, then the above method is modified as follows:
(a) applying a suitable potential between the electrodes;
(b) adding the substrate of said biocatalyst;
(c) measuring a background current;
(d) contacting the biosensor with the sample containing the inhibiting-analyte;
(e) measuring a current change that is proportional to the inhibiting-analyte concentration;
(f) optionally subtracting from the value obtained in (d) the current change measured with a blank electrode.

Step (c) is carried out either by adding a drop of the sample containing the inhibiting-analyte to the biosensor or by immersing the sample in the solution. This method can be further used to determine the enzymatic activities. In such case, the current changes must be measured as time-dependent. The present invention will now be illustrated with the following experimental examples, having no limitative function.

EXPERIMENTAL PART

Example 1

Current Change Variation with pH in the Presence of Dissolved Hematein by Using a Platinum Electrode Hematein (Fluka, Cat. No. 51230) is dissolved in 0.05 M phosphate buffer containing 0.1 M sodium chloride. The working platinum electrode and the SCE reference electrode are immersed in the solution and the current is measured by an Amel 559 amperometric detector (Amel Instruments, Milano, Italy) at the constant potential of 0.0 mV. The pH value decreases as 2M sulphuric acid aliquots are added and the corresponding current change is monitored. Meanwhile, the pH is measured by pH-meter (PHM 85, Radiometer, Copenhagen, Denmark). The relationship between the current change and the pH for two concentrations of hematein (0.5 mM—curve a; and 2.5 mM—curve b) is illustrated in FIG. 1.

Example 2

Figure 2:
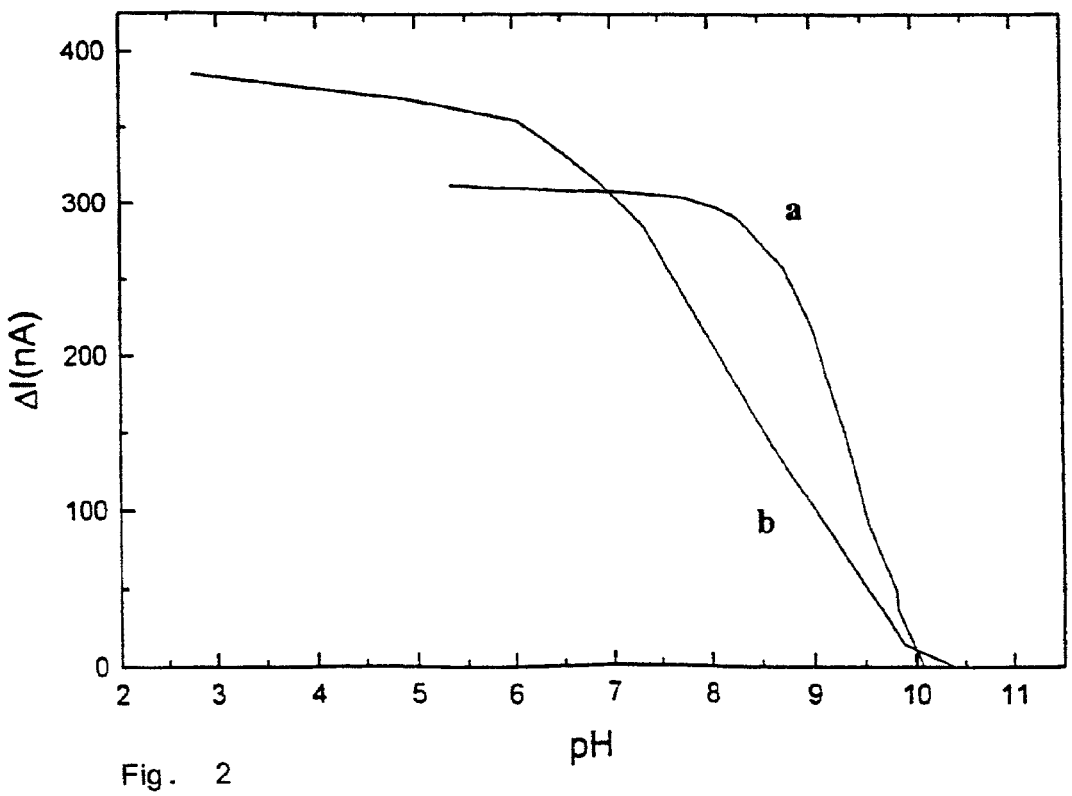

Current Change Variation with pH in the Presence of Dissolved Hematein by Using Composite Electrodes The carbon paste electrode is prepared by mixing, under vigorous stirring, 7 parts (w/w) of graphite (Fluka, Cat. No. 50870) with 3 parts (w/w) of paraffin oil (Fluka, Cat. No. 76235) in a mortar. The mixture is introduced into a plastic tube (inner diameter: 2 mm) equipped with a brass rod. The solid composite electrode is prepared by mixing vigorously 2 parts (w/w) of graphite with 3 parts (w/w) of melted n-eicosane (Sigma, Cat. No. E-9752) at 45° C. This mixture is introduced into a plastic tube (inner diameter: 2 mm) equipped with a brass rod. Both electrodes are smoothed with a sheet of paper before use. The electrochemical measurements are carried out as described in Example 1 with 0.5 mM hematein and the current changes obtained are reported in FIG. 2 (curve a—carbon paste electrode, curve b—solid composite electrode)

Example 3

Current Change Variation with pH by Using a Golden Electrode Modified with Methylene Blue.

Figure 3:
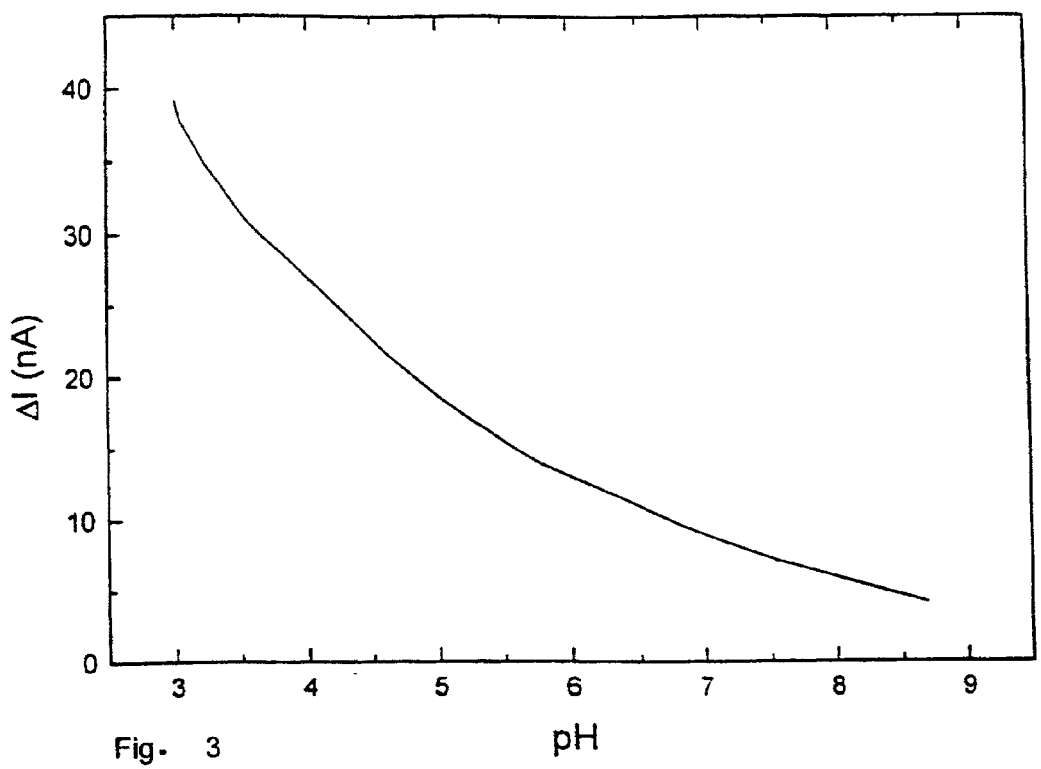

The newly polished golden electrode (Amel Instruments) is immersed in a 0.5 mM methylene blue solution (Aldrich, Cat. No. 86, 124-3) for 12 hours. Then, the electrode is accurately rinsed with deionized water. The electrochemical measurements are carried out as described in Example n.1, by using a working potential of −100 mV (versus SCE). The results are reported in FIG. 3.

Example 4

Current changes variation with pH by using a solid composite electrode in the presence of dissolved hematoxylin, quercitin and harmaline.

Figure 4:
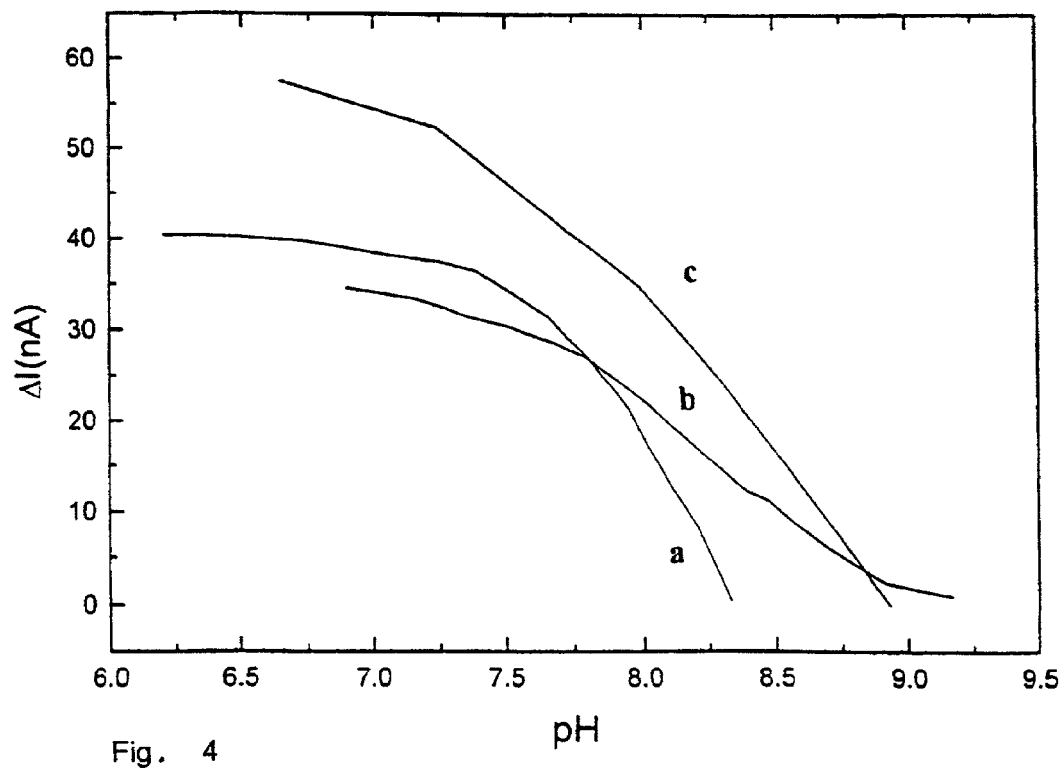

The solid composite electrodes are prepared as described in Example 2. The pH is measured in 0.5 mM solutions of hematoxylin, quercitin, harmaline by using the buffer described in Example n. 1. The working potential for hematoxylin and quercitin is 0.0 mV (versus SCE), while for harmaline is 600 mV. The results are illustrated in FIG. 4 (curve a—hematoxylin; curve b—quercitin; curve c—harmaline).

Example 5

Current Change Variation with pH by Using a Solid Composite Electrode the Surface of Which has been Modified with a poly(ortho-phenylendiamine) Film.

Figure 5:
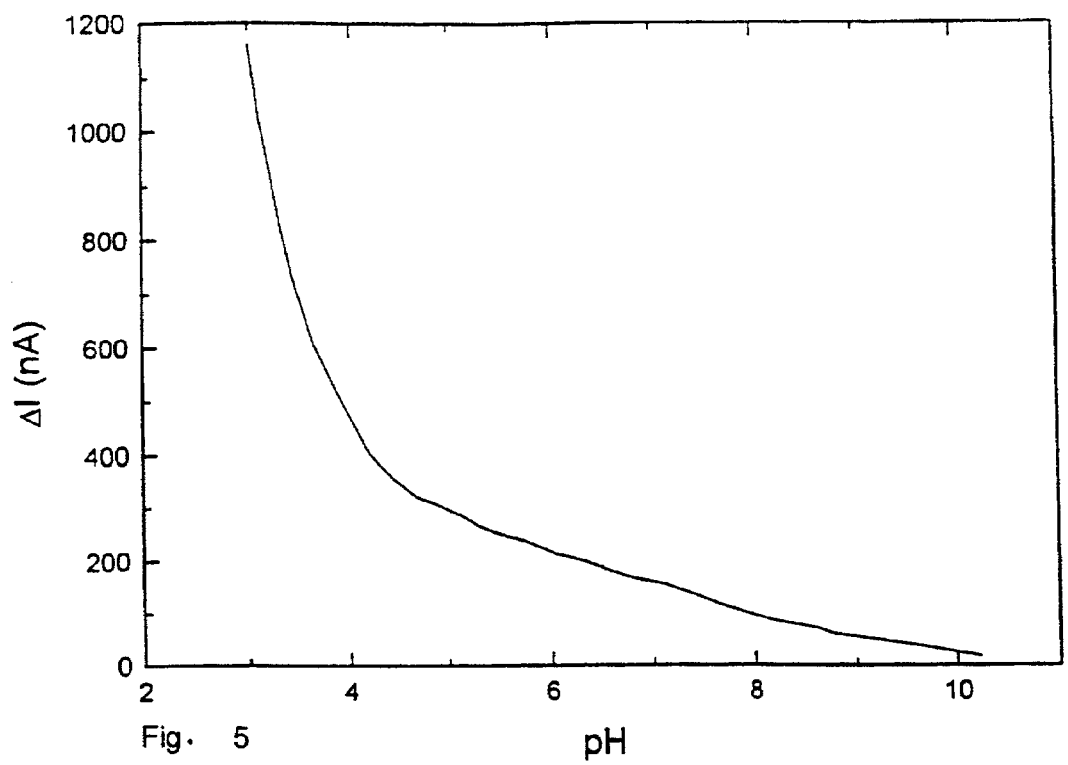

The solid composite electrode is prepared by mixing vigorously graphite with melted n-eicosane (weight ratio 1:1) at 45° C. The mixture obtained in this way is introduced into a plastic tube (inner diameter 2 mm) equipped with a brass rod. A poly-(ortho-phenylendiamine) film is deposited onto the polished electrode surface by means of electrochemical polymerization of ortho-phenylendiamine monomer (Sigma, Cat. No. P-9029) in aqueous solution. This process is carried out in the following way: the scanning of the electrode potential is repeated 30 times from—0.5 mV to 0.7 mV (versus SCE) at 50 mVs$_{-1}$ in oxygen-free 0.1 mM acetate buffer at pH 5.0 which contains 0.5 mM ortho-phenylendiamine under inert atmosphere. The modified electrode is then thoroughly rinsed with the phosphate buffer. This biosensor is then tested at different pH values of a solution and the current change is measured according to the procedure described in Example 1. The working potential is −600 mV. The results are illustrated in FIG. 5.

Example 6

Current Change Variation for a Platinum Electrode the Surface of Which is Modified with Polypyrogallol.

Figure 6:
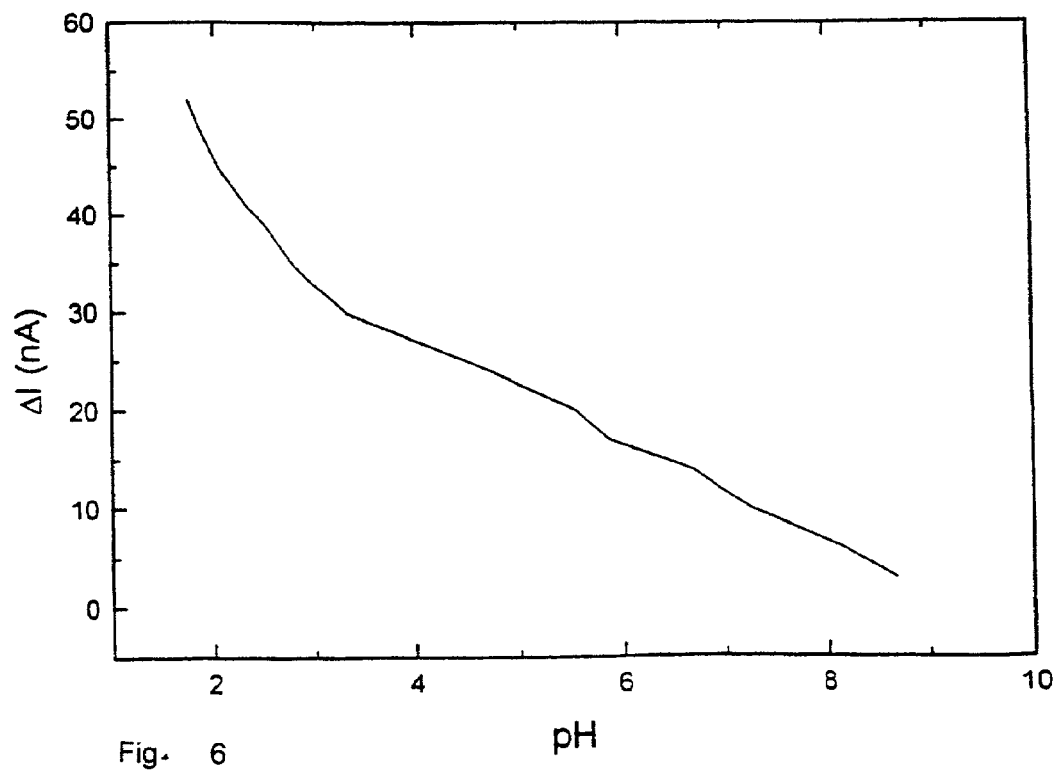

The polypyrogallol film is deposited upon the newly polished surface of the platinum electrode by electrochemical polymerization of 25 mM of pyrogallol (Aldrich, Cat. Mo. 25.400-2) in aqueous solution containing 0.15 M phosphate buffer (pH 7.0) and tetraethylamonium tetrafluoroborate 0.1 M (Aldrich, Cat. No. 24, 214-4). The scanning of the potential electrode is repeated three times from 0.0 V and 1.1 V (versus SCE) at 50 mVs$^{-1}$. The modified electrode is then rinsed thoroughly with the phosphate buffer. This biosensor is tested at the different pH values of a solution and the current change is measured with the same procedure as described in Example n. 1. The working potential is 200 mV. The results are shown in FIG. 6.

Example 7

Variation of the Current Changes for a Solid Composite Electrode Modified with Lauryl Gallate.

Figure 7:
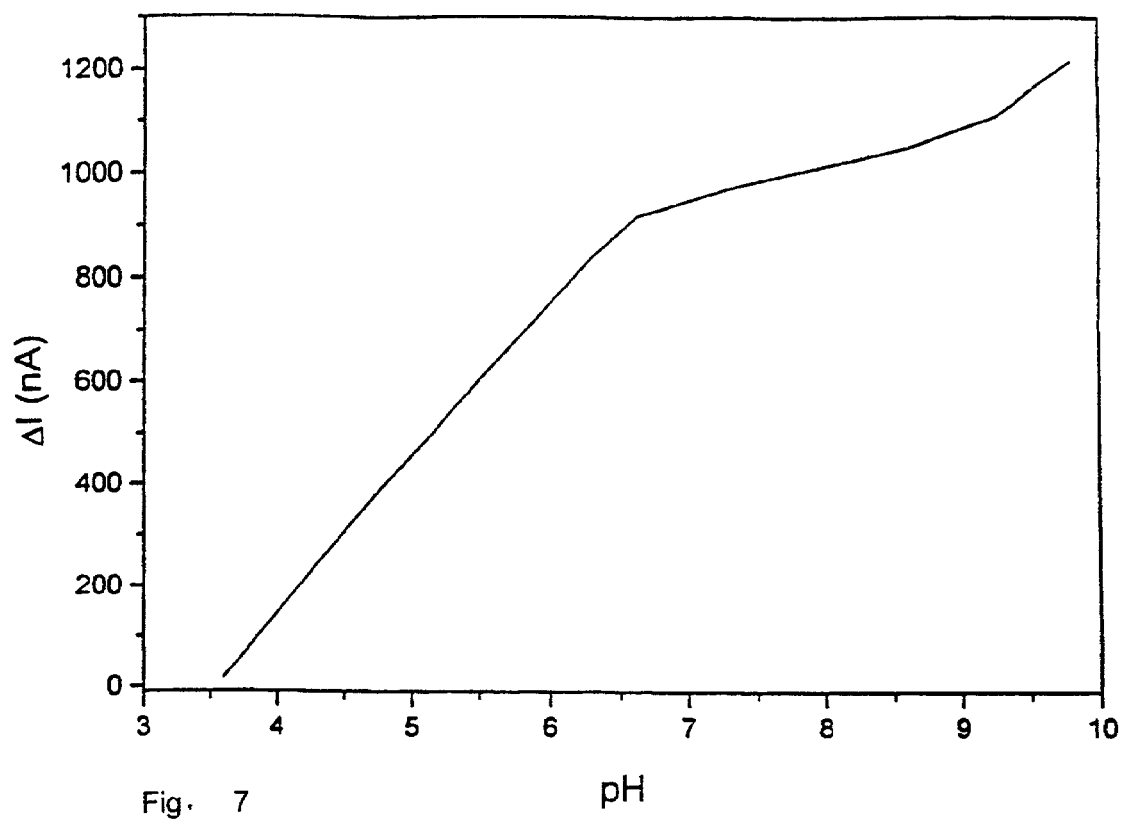

The graphite powder is modified as follows: 100 mg of lauryl gallate (Fluka, Cat. No. 48660) are dissolved in 2 ml of acetone and 400 mg of modified graphite are added to the solution. The mixture is stirred up to being made homogeneous and acetone is then evaporated under forced air flow at room temperature. 100 mg of lauric acid (Fluka, Cat. Mo. 61610) and 150 mg of 2-hexadecanone (Fluka, Cat. No. 69250) are dissolved in a porcelain dish at 50° C. and stirred vigorously with 250 mg of the modified graphite. A plastic tube (inner diameter 2 mm) equipped with a brass rod is filled with this mixture; the electrode material then solidifies at room temperature. The electrode surface is smoothed with sand paper and cleansed with a sheet of common paper. The current change dependence on the pH of the electrode modified by lauryl gallate is measured with the same procedure as the one described in Example n.1. The working potential is 200 mV. The results are illustrated in FIG. 7.

Example 8

Preparation of the Biosensor for the Determination of Urea Based on a Platinum Electrode Modified with Urease and Dissolved Hematein A solution (2 μl, 10 mg/ml) of urease (EC 3.5.1.5., Sigma, Cat. No. U-0376) is applied onto the surface of the platinum electrode. After drying at room temperature, the electrode is covered with a dialysis membrane (Spectra/Por MWCO 6,000–8,000), fixed by means of an O-ring. The biosensor is immersed in 1 mM phosphate buffer (pH=7.35) containing 0.5 mM hematein and 0.1 mM sodium chloride. Hence, the biosensor is polarized at 0.0 mV (versus SCE) and a few aliquots of urea solution (5 mg/ml) are added to the measuring buffer. The relationship between the urea concentration and the current change is reported in FIG. 8 (curve a).

Example 9

Preparation of the Biosensor for the Determination of Urea Based on the Solid Composite Electrode Modified with Urease and Dissolved Hematein.

Figure 8:
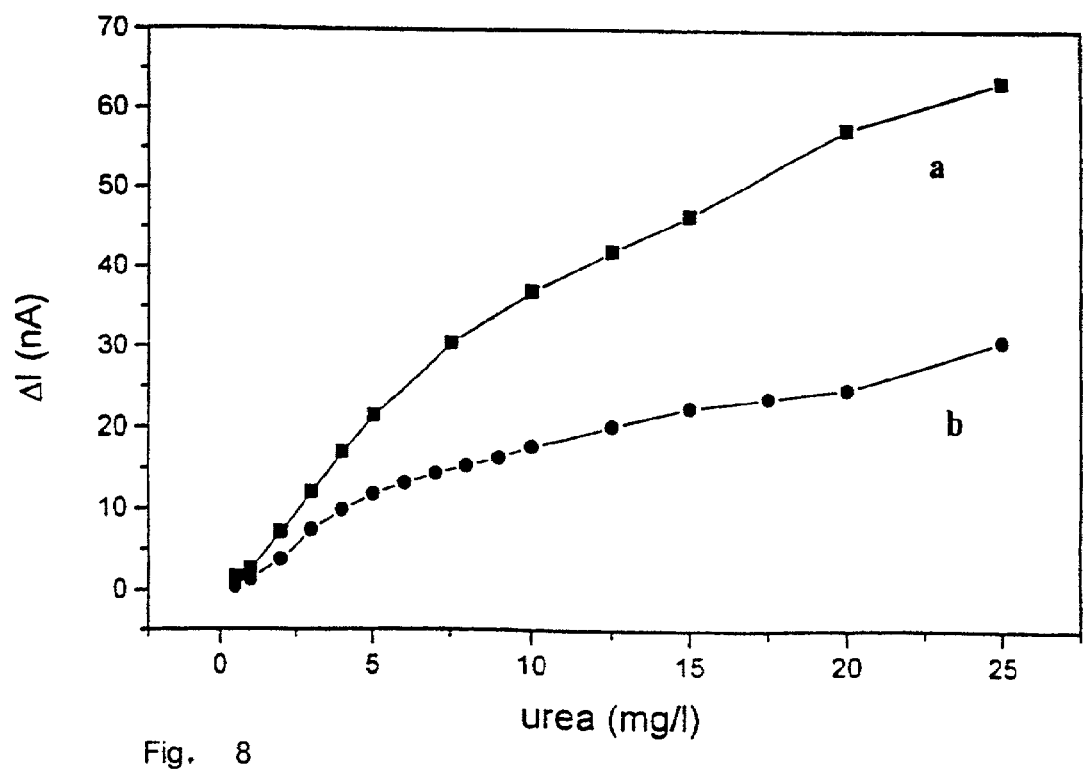
FIGS. 8–16 show the calibration curves of several analytes measured with the biosensors of the invention as described in the Examples 8–17.

The solid composite electrode is prepared as described in Example 2. Urease (2 μl, 10 mg) is applied onto the clean electrode surface. After drying, the electrode is covered with a dialysis membrane (Spectra/por MWCO 6,000–8,000) by means of an O-ring. The biosensor is then immersed in 1 mM phosphate buffer (pH=7.35) containing 0.5 mM hematein and 0.1 M sodium chloride. The electrode is then polarized at 0.0 mV (versus SCE). A few aliquots of urea standard solutions (5 mg/ml) are added to the measuring buffer. The relationship between the urea concentration and the current change is shown in FIG. 8 (curve b).

Example 10

Figure 9:
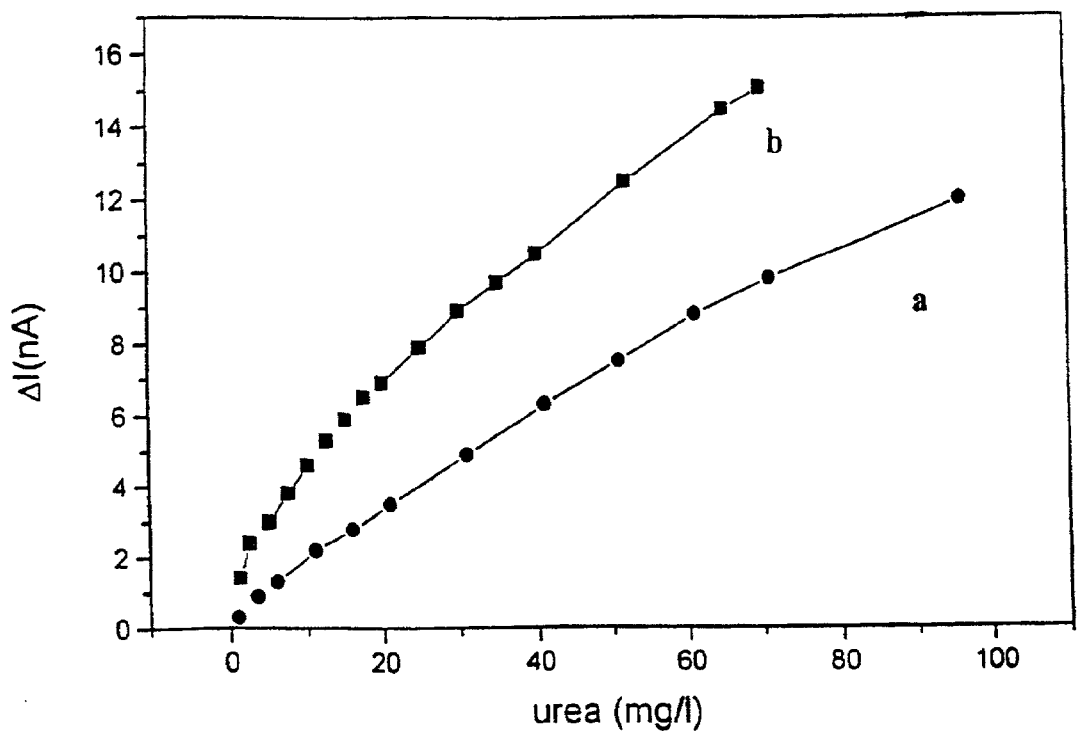

Preparation of the Biosensor for Detection of Urea Based on the Bulk Modified Solid Composite Electrode and Dissolved Hematein The graphite powder is modified in the following way: 97 mg of graphite powder are added to 0.5 ml urease aqueous solution (6 mg/ml). The mixture is accurately mixed to obtaining a homogeneous mixture and water is then gently evaporated. 50 mg of the modified graphite are mixed with 50 mg of 2-hexadecanone at 50° C. and the mixture obtained is poured into a plastic tube (inner diameter 2 mm) equipped with a brass rod; the mixture is then cooled down at room temperature. The electrode is smoothed with a sheet of paper and covered with a dialysis membrane (Spectra/Por MWCO 6,000–8,000). The biosensor is immersed in the phosphate buffer (1 or 5 mM, pH 7.50) containing 0.5 mM hematein and 0.1 M sodium chloride. It is then polarized at 0.0 mV (versus SCE). A few aliquots of urea standard solution (5 mg/ml) are added to the measuring buffer. The current changes are recorded and the results are illustrated in FIG. 9, where curve b) refers to 1 mM phosphate buffer.

Example 11

Preparation of the Biosensor for the Determination of Urea by Using a Solid Composite Electrode Modified with Urease and Containing Lauryl Gallate.

Figure 10:
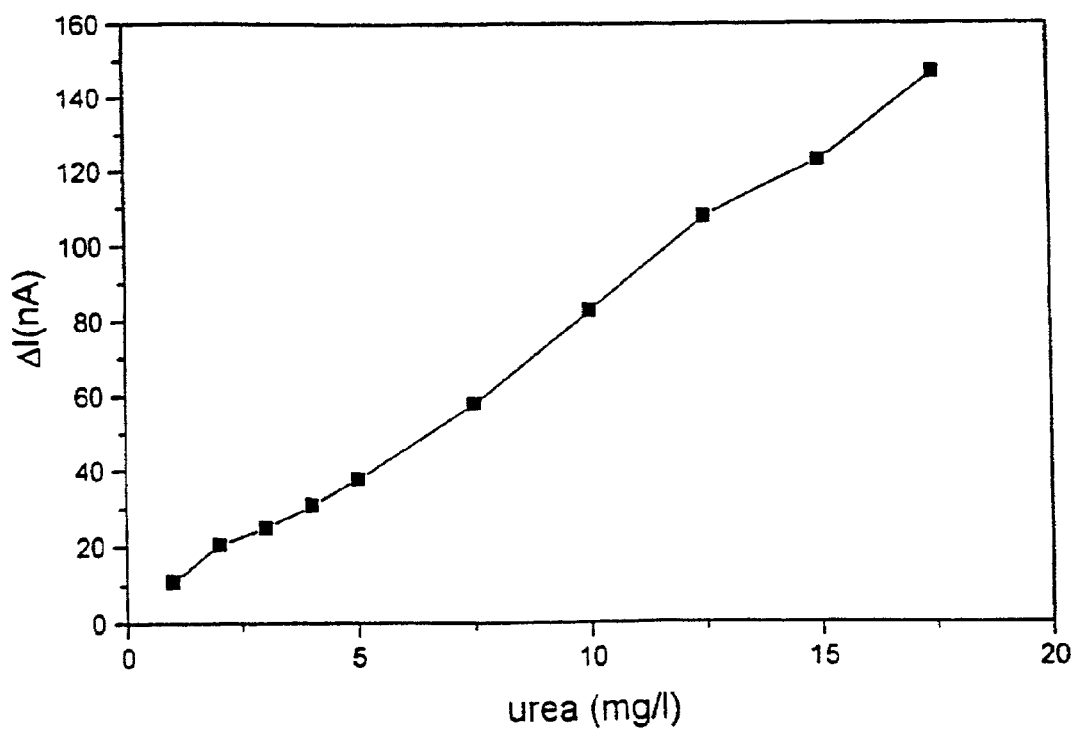

The graphite powder is modified in the following way: 20 mg of lauryl gallate are dissolved in 0.5 ml of acetone and 90 mg of graphite are added to the solution. The mixture then is stirred up to making it homogeneous and acetone is evaporated under forced air at room temperature. 40 mg of 2-hexadecanone and 5 mg of stearic acid (Aldrich, Cat. No. 26, 838-0) are dissolved in a porcelain dish at 55° C. and mixed vigorously with 55 mg of the modified graphite quoted above. The mixture is then poured into a plastic tube (inner diameter: 2 mm) equipped with a brass rod. Urease (1 μl, 30 mg/ml) is applied onto the newly cleansed electrode surface. After drying, the electrode is covered with a dialysis membrane (Spectra/Por MWCO 6,000–8,000) fixed with an O-ring. The biosensor is immersed in 1 mM phosphate buffer (pH 7.35 containing 0.1 M sodium chloride). It is then polarized at 200 mV (versus SCE). Then several aliquots of standard solutions of urea (5 mg/ml) are added to the measuring buffer. The current changes are recorded. The relationship between the urea concentration and the current change is illustrated in FIG. 10.

This biosensor allows to perform 30 reproducibile measurements.

This biosensor is tested after storage in dried state at temperature of 22±2° C. under controlled umidity (<0.5%). After 6 month the sensitivity variation is not significant (<3%).

Example 12

Preparation of the Biosensor for the Determination of Oxalacetate by Using a Solid Composite Electrode Modified with Oxalacetate Decarboxylase and Dissolved Hematein.

Figure 11:
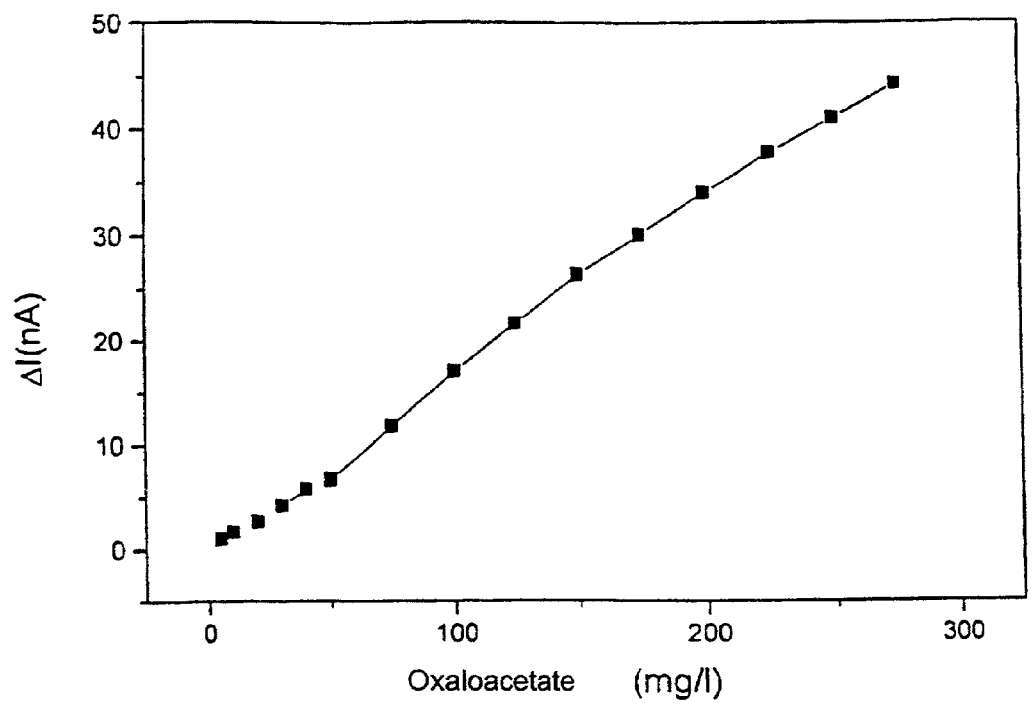

The solid composite electrode is described in Example n. 2. The oxalacetate decarboxylase (EC 4.1.1.3., ICN, Cat. No. 156007, 5,3 U) is applied onto the electrode surface. After drying, the electrode is covered with a dialysis membrane (Spectra/Por MWCO 6,000–8,000) fixed by means of an O-ring. The biosensor is then plunged into 1 mM phosphate buffer (pH 8.0) containing 0.5 mM hematein and 0.1 M sodium chloride. It is then polarized at 0.0 mV (versus SCE). Several aliquots of standard solutions of sodium oxalacetate (20 mg/ml) are added to the measuring buffer. The current changes are recorded. The relationship between the oxalacetate concentration and the current change is shown in FIG. 11.

Example 13

Preparation of the Biosensor Based on a Solid Composite Electrode Modified with Glucose Oxidase and Covered with a Poly(Para-Phenylendiamine) Film.

Figure 12:
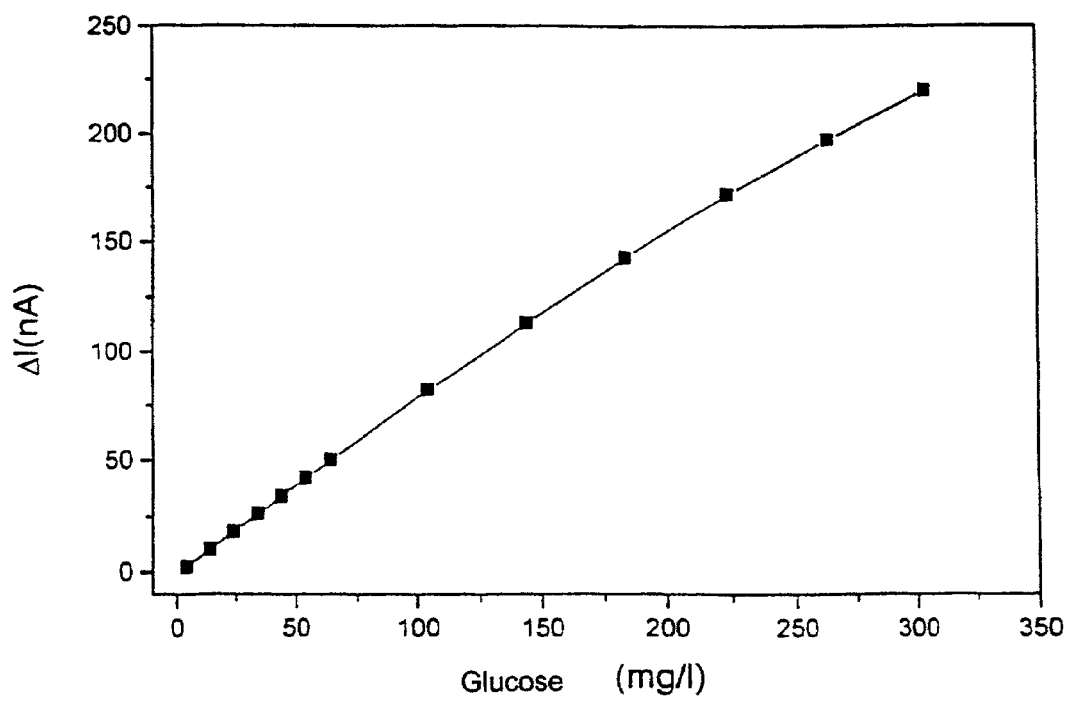

The solid composite electrode with the thick poly(para-phenylendiamine) film is prepared as described in Example N.5. The glucose oxidase (EC 1.1.3.4, Sigma, Cat. No. G-7016, 2 μl, 10 mg/ml) is applied onto the electrode surface that is then rinsed and covered with a dialysis membrane (Spectra/Por MWCO 6,000–8,000) fixed with an O-ring. The biosensor is then immersed in a phosphate buffer (1 mM, pH 7.0) containing 0.1 M sodium chloride. It si then polarized at −600 mV (versus SCE). Several aliquots of glucose standard solutions (20 mg/ml) are added to the measuring buffer. The current changes are recorded. The relationship between the glucose concentration and the current change is shown in FIG. 12.

Example 14

Preparation of the Biosensor for the Determination of Hydrogen Carbonate Based on a Platinum Electrode Modified with Carbonic Anhydrase and Dissolved Hematein.

Figure 13:
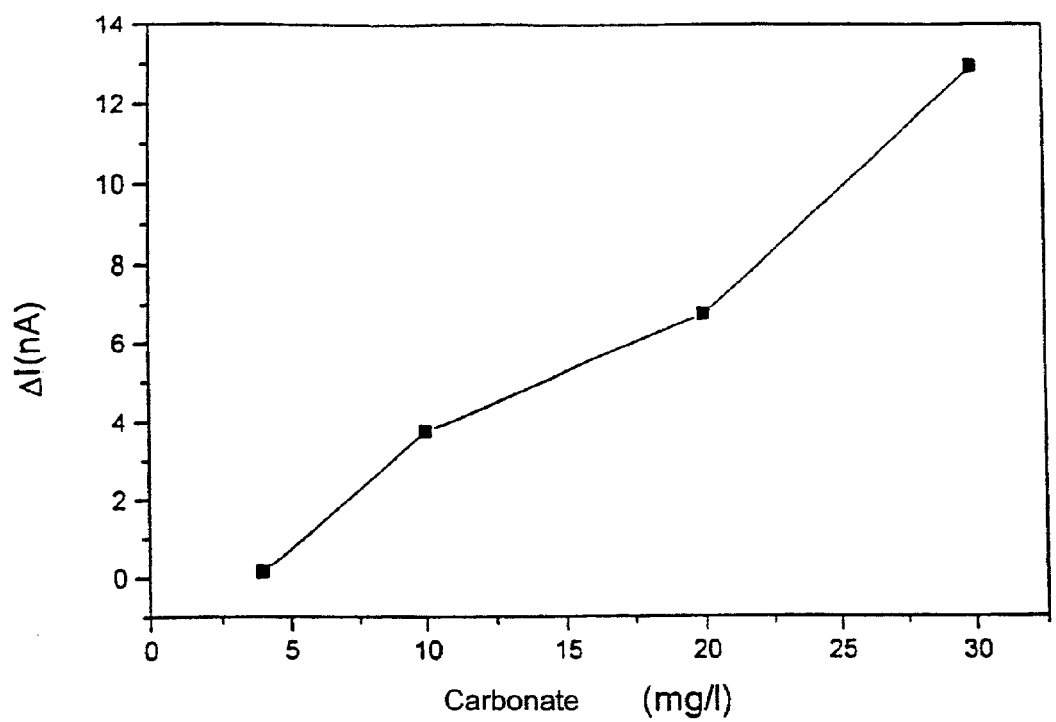

A solution of carbonic anhydrase (EC 4.2.1.1, Sigma, Cat. No. C 4831, 2400 W-A units, 2 μl, 100 mg/ml) is applied onto the surface of the platinum electrode. After drying, the electrode is covered with a dialysis membrane (Spectra/Por MWCO 6,000–8,000) fixed by means of an O-ring. The biosensor is then immersed in Tris-HCl 4 mM (pH 8.30) containing 0.5 mM hematein and sodium chloride. It is then polarized at 0.0 mV (versus SCE). A few aliquots of sodium hydrogen- carbonate standard solutions (10 mg/ml) are added to the measuring buffer. The relationship between the concentration of hydrogen carbonate and the current change is shown in FIG. 13.

Example 15

Preparation of the Biosensor Based on a Platinum Working Electrode Modified with Penicillinase and Dissolved Hematein.

Figure 14:
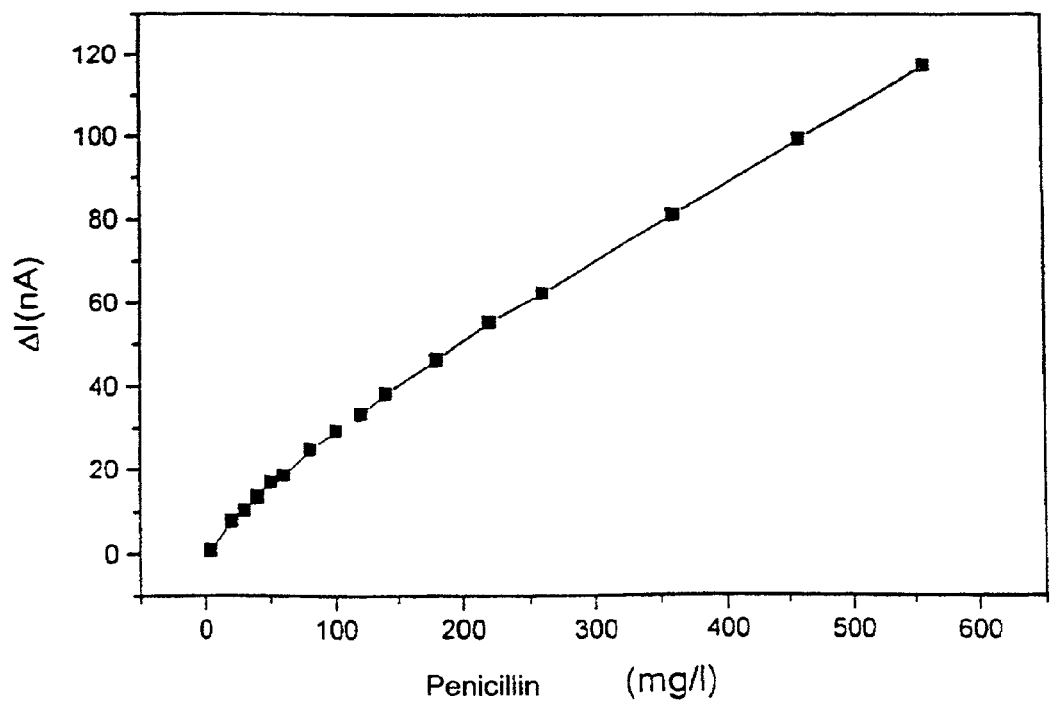

A solution (2 μl, 100 mg/ml) of penicillinase (EC 3.5.2.6, Sigma, Cat. No P-0389) is applied onto the platinum electrode surface. After having dried it at room temperature, the electrode is covered with a dialysis membrane (Spectra/Por MWCO 6,000–8,000) fixed by an O-ring. The biosensor is then immersed in 1 mM phosphate buffer (pH=7.5) containing 0.5 mM hematein and 0.1 M sodium chloride. It is then polarized at 0.0 mV (versus SCE). A few aliquots of standard solutions of benzylpenicilline sodium salt (20 mg/ml) are added to the measuring solution. The current changes are recorded. The relationship between the benzylpenicilline and the current change is illustrated in FIG. 14.

Example 16

Preparation of the Biosensor for ATP Determination Based on a Platinum Working Electrode Modified with Apyrase and Dissolved Hematein.

Figure 15:
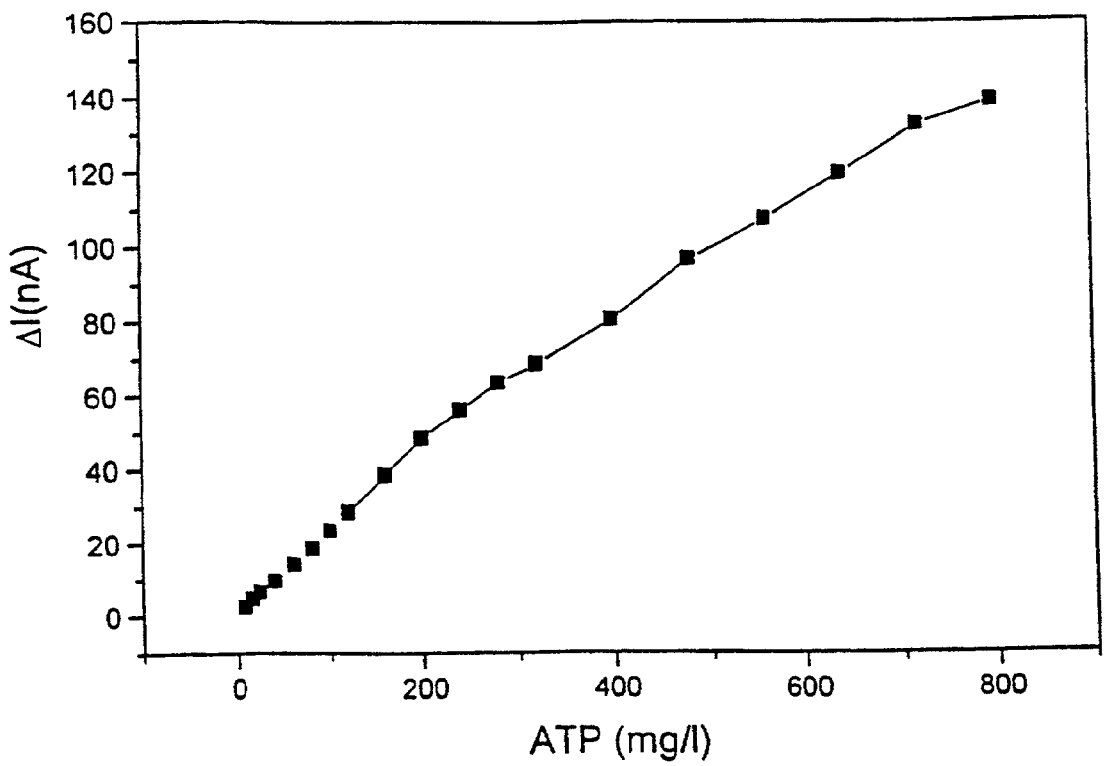

One solution (2 μl, 200 mg/ml) of apyrase (EC 3.6.1.5, Sigma, Cat. No A-6132) is applied onto the platinum electrode surface. After having dried it at room temperature, the electrode is covered with a dialysis membrane (Spectra/Por MWCO 6,000–8,000) fixed by an O-ring. The biosensor is immersed in Tris-HCl 2 mM (pH=7.0) containing 0.5 mM of hematein and 0.25 of sodium chloride. It is then polarized at 0.0 mV (versus SCE). Several aliquots of standard solutions of ATP sodium salt (20/ml) are added to the measuring buffer. The current changes are recorded. The relationship between the ATP concentration and the current change is illustrated in FIG. 15.

Example 17

Figure 16:
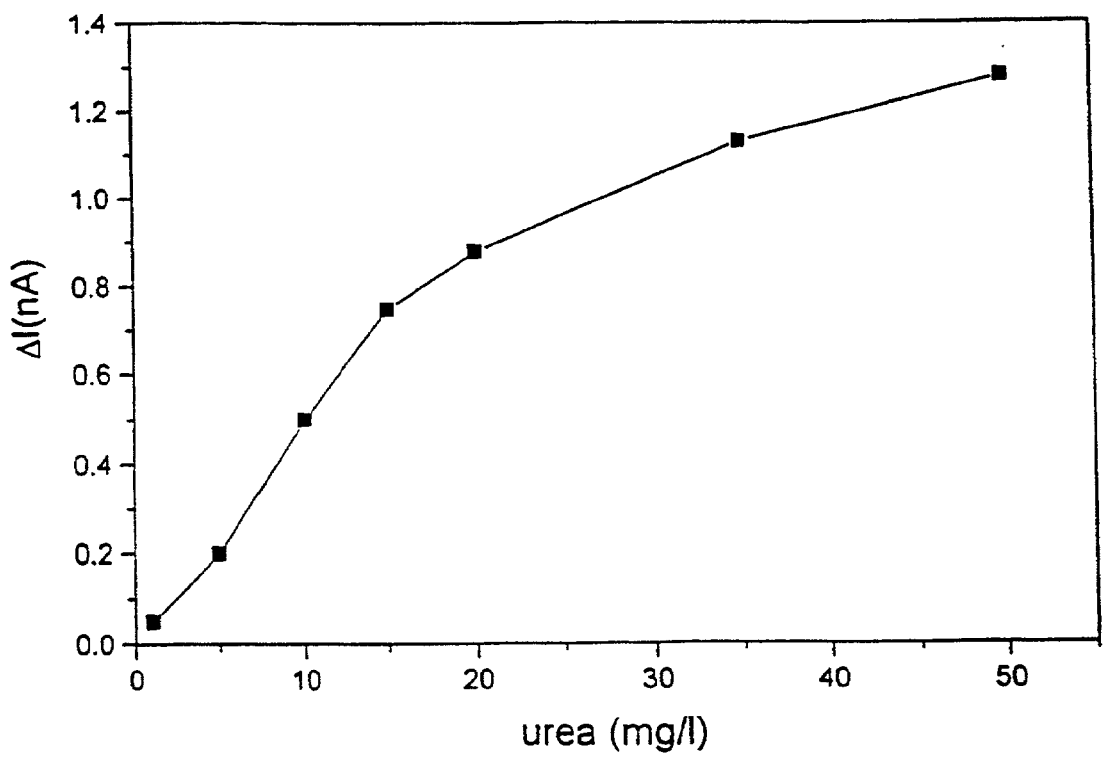

Preparation of the Biosensor for Urea Determination Based on a Golden Electrode Modified with Methylene Blue The electrode is prepared as described in Example n. 3. Urease (3 μl, 10 mg/ml) is applied onto the electrode surface. After drying, the electrode is covered with a dialysis membrane (Spectra/Por MWCO 6,000–8,000) fixed by an O-ring. The biosensor is immersed in 1 mM phosphate buffer (pH=7.50) containing 0.1 M sodium chloride. It is then polarized at −100 mV (versus SCE). A few aliquots of urea standard solution (5 mg/ml) are added to the measuring buffer. The current changes are recorded. The relationship between the urea concentration and the current change is shown in FIG. 16.

The invention claimed is:

1. An amperometric biosensor system for the detection of analytes comprising:
   a) at least one biocatalyst producing a pH change by its interaction with the analyte; the biocatalyst not belonging to a group of oxidoreductase enzymes;
   b) at least one pH-sensitive redox compound, in the form of a monomer, exhibiting different redox properties in its protonated and non-protonated forms selected from the group consisting of cyclic hydrocarbons, containing from 4 to 30 carbon atoms and substituted with at least one group selected from —OH, —SH, —NH$_2$, =O, =S, =NH, —OR$_1$, —SR$_1$, —NHR$_1$, —NR$_1$R$_2$, and =NR$_1$, wherein R$_1$ and R$_2$ are hydrocarbon chains optionally further substituted, or selected from the group consisting of heterocyclic compounds containing from 3 to 30 carbon atoms and one or more heteratoms selected from the group consisting of N, S, O, Se, Te, B, P, As, Sb, and Si, optionally substituted with a group selected for —OH, —SH, —NH$_2$, =O, =S, —NH, —OR, —SR$_1$, —NHR$_1$, —NR$_1$R$_2$, and =NR$_1$, wherein R$_1$ and R$_2$ are independent hydrocarbon chains;
   c) a working electrode; and
   d) a reference electrode;
   e) the electrodes being connected through an ammeter.

2. The biosensor system according to claim 1, wherein the biocatalyst is selected from the group consisting of enzymes, synzymes, cells, cell components, tissues, imunoproteins, nucleic acids and extracts, fractions, fragments, homogenates, and lysates thereof.

3. The biosensor system according to claim 2, wherein the enzyme is selected from the group consisting of hydrolase, transferase, lyase, and ligase.

4. The biosensor system according to claim 2, wherein the enzyme is selected from the group consisting of phosophorylase, decarboxylase, esterase, phosphatase, and deaminase.

5. The biosensor system according to claim 2, wherein the enzyme is selected from the group consisting of urease, oxalacetate decarboxylase, carbonic anhydrase, penicillinase, and apyrase.

6. The biosensor system according to claim 1, wherein the pH-sensitive redox compound is a pH indicator.

7. The biosensor system according to claim 6, wherein the pH indicator is selected from the group consisting of phenoxazines, phenothizines dyes, and natural antioxidants.

8. The biosensor system according to claim 1, wherein the pH-sensitive redox compound is selected from the group consisting of hematoxylin, hematein, methylene blue, quercitin, flavonoids, alkyl gallates and para-phenylendiamine.

9. The biosensor system according to claim 1, wherein the working electrode is a solid composite electrode, platinum electrode, gold electrode, mercury electrode or glassy carbon electrode.

10. The biosensor system according to claim 1, wherein the reference electrode is selected from the group consisting of Ag/AgCl and calomel electrodes.

11. A method for detecting analytes consisting in:
    (a) providing an amperometric biosensor system comprising:
       (i) at least one biocatalyst producing a pH change by its interaction with the analyte; the biocatalyst not belonging to a group of oxidoreductase enzymes; the biocatalyst being inhibited by the analyte;
       (ii) at least one pH-sensitive redox compound exhibiting different redox properties in its protonated and non-protonated forms selected from the group consisting of cyclic hydrocarbons, containing from 4 to 30 carbon atoms and substituted with at least one group selected from —OH, —SH, —NH$_2$, =O, =S, =NH, —OR$_1$, —SR$_1$, —NHR$_1$, —NR$_1$R$_2$, and =NR$_1$, wherein R$_1$ and R$_2$ are hydrocarbon chains optionally further substituted, or selected from the group consisting of heterocyclic compounds containing from 3 to 30 carbon atoms and one or more heteratoms selected from the group consisting of N, S, O, Se, Te, B, P, As, Sb, and Si, optionally substituted with a group selected for —OH, —SH, —NH$_2$, =O, =S, —NH, —OR, —SR$_1$, —NHR$_1$, —NR$_1$R$_2$, and =NR$_1$, wherein R$_1$ and R$_2$ are independent hydrocarbon chains;
       (iii) a working electrode; and
       (iv) a reference electrode;
       (v) the electrodes being connected through an ammeter;
    (b) placing the electrodes in a measuring solution;
    (c) applying a suitable potential between the electrodes;
    (d) adding the substrate of the biocatalyst to the measuring solution;
    (e) measuring a background current;
    (f) adding to the solution the sample containing the inhibiting-analyte to be determined;
    (g) measuring a current change that is proportional to the inhibiting-analyte concentration; and
    (h) optionally subtracting the current change measured with a blank electrode from the value obtained in (g).

12. A method for detecting analytes consisting in:

(a) providing an amperometric biosensor system comprising:
- (i) at least one biocatalyst producing a pH change by its interaction with the analyte; the biocatalyst not belonging to a group of oxidoreductase enzymes; the biocatalyst being inhibited by the analyte;
- (ii) at least one pH-sensitive redox compound exhibiting different redox properties in its protonated and non-protonated forms selected from the group consisting of cyclic hydrocarbons, containing from 4 to 30 carbon atoms and substituted with at least one group selected from —OH, —SH, —NH$_2$, =O, =S, =NH, —OR$_1$, —SR$_1$, —NHR$_1$, —NR$_1$R$_2$, and =NR$_1$, wherein R$_1$ and R$_2$ are hydrocarbon chains optionally further substituted, or selected from the group consisting of heterocyclic compounds containing from 3 to 30 carbon atoms and one or more heteroatoms selected from group consisting of N, S, O, Se, Te, B, P, As, Sb, and Si, optionally substituted with a group selected for —OH, —SH, —NH$_2$, =O, =S, —NH, —OR, —SR$_1$, —NHR$_1$, —NR$_1$R$_2$, and =NR$_1$, wherein R$_1$ and R$_2$ are independent hydrocarbon chains;
- (iii) a working electrode; and
- (iv) a reference electrode;
- (v) the electrodes being connected through an ammeter;

(b) applying a suitable potential between the electrodes;

(c) adding the substrate of the biocatalyst;

(d) measuring a background current;

(e) contacting the biosensor with the sample containing the inhibiting-analyte system;

(f) measuring a current change that is proportional to the inhibiting-analyte concentration; and (g) optionally subtracting the current change measured with a blank electrode from the value obtained in (f).

* * * * *